United States Patent
Carlsson et al.

(10) Patent No.: US 11,944,684 B2
(45) Date of Patent: Apr. 2, 2024

(54) COMPOSITION FOR TREATING AND/OR PREVENTING FUNGAL INFECTIONS

(71) Applicant: PEPTONIC MEDICAL AB, Bromma (SE)

(72) Inventors: Anders Carlsson, Stockholm (SE); Dan Markusson, Växjö (SE)

(73) Assignee: PEPTONIC MEDICAL AB, Bromma (SE)

( * ) Notice: Subject to any disclaimer, the term of this patent is extended or adjusted under 35 U.S.C. 154(b) by 0 days.

(21) Appl. No.: 18/251,929

(22) PCT Filed: Nov. 5, 2021

(86) PCT No.: PCT/EP2021/080740
§ 371 (c)(1),
(2) Date: May 5, 2023

(87) PCT Pub. No.: WO2022/096632
PCT Pub. Date: May 12, 2022

(65) Prior Publication Data
US 2023/0321247 A1    Oct. 12, 2023

(30) Foreign Application Priority Data

Nov. 9, 2020   (SE) .................................... 2051299-2

(51) Int. Cl.
| | | |
|---|---|---|
| A61K 47/38 | (2006.01) | |
| A61K 31/192 | (2006.01) | |
| A61P 31/04 | (2006.01) | |
| A61P 31/10 | (2006.01) | |
| A61K 9/08 | (2006.01) | |

(52) U.S. Cl.
CPC ............ *A61K 47/38* (2013.01); *A61K 31/192* (2013.01); *A61P 31/04* (2018.01); *A61P 31/10* (2018.01); *A61K 9/08* (2013.01)

(58) Field of Classification Search
CPC ........ A61K 47/38; A61K 31/192; A61K 9/08; A61K 31/19; A61P 31/04; A61P 31/10
See application file for complete search history.

(56) References Cited

U.S. PATENT DOCUMENTS

| | | | |
|---|---|---|---|
| 9,913,871 B2 * | 3/2018 | Ellington | ................. A61P 15/18 |
| 2017/0233798 A1* | 8/2017 | Neely | ................. G01N 24/088 435/5 |
| 2017/0296610 A1 | 10/2017 | Ellington et al. | |

FOREIGN PATENT DOCUMENTS

| | | |
|---|---|---|
| WO | WO 2012/040224 A2 | 3/2012 |
| WO | WO 2018/219747 A1 | 12/2018 |

OTHER PUBLICATIONS

Thaker et al. (Indian J Pharmacol., 2013, 45(6), 622-624). (Year: 2013).*
Handbook of pharmaceutical excipients, Benzoic Acid ED—Rowe RC; Sheskey P J; Owen SC, Jan. 1, 2006, Handbook of pharmaceutical Excipients, Fifth Edition.
Hypromellose in: Handbook of Pharmaceutical Excipients—Rowe RC; Sheskey P J; Owen SC, Jan. 1, 2006, Handbook of pharmaceutical Excipients.
International Search Report and Written Opinion were dated Feb. 22, 2022 by the International Searching Authority for International Application No. PCT/EP2021/080740 filed on Nov. 5, 2021 and published as WO 2022/096632 (Applicant—Peptonic Medical AB) (10 pages).
International Preliminary Report on Patentability was dated Oct. 10, 2022 by the European Patent Office for International Application No. PCT/EP2021/080740 filed on Nov. 5, 2021 and published as WO 2022/096632 (Applicant—Peptonic Medical AB) (17 pages).

* cited by examiner

*Primary Examiner* — Genevieve S Alley
(74) *Attorney, Agent, or Firm* — Ballard Spahr LLP

(57) ABSTRACT

Described is an aqueous composition comprising:
(a) at least one non-ionic cellulose ether, and
(b) benzoic acid within the range of from 0.2 wt % to 0.3 wt % based on the total weight of the composition,
wherein said composition has a viscosity equal to or above 24 000 cP, an osmolality of from 100 to 400 mOsmol/kg, and a pH of from 3 to 5. The aqueous composition may be used in the treatment and/or prevention of a human fungal infection such as a vaginal fungal infection.

15 Claims, No Drawings

COMPOSITION FOR TREATING AND/OR PREVENTING FUNGAL INFECTIONS

CROSS-REFERENCE TO RELATED APPLICATIONS

This application is a U.S. National Phase Application of International Application No. PCT/EP2021/080740, filed Nov. 5, 2021, which claims the benefit to Swedish Application No. 2051299-2, filed Nov. 9, 2020, each of which are hereby incorporated by reference in their entirety.

TECHNICAL FIELD

The present document is directed to a composition for use in the treatment and/or prevention of human fungal infections such as genital fungal infection, urinary tract infection, oral fungal infection, skin fungal infection and/or nail infection. In particular, the composition may be used in the treatment and/or prevention of a genital fungal infection such as a vaginal fungal infection.

BACKGROUND

Fungi are one of four major groups of microorganisms, namely bacteria, viruses, parasites and fungi. While most fungi are not associated with human disease, there are about 20 to 25 species of fungi that are common causes of infection.

Fungal infections involve invasion of body tissues by one or more species of fungi and may take place superficially, locally and/or systemically. A fungal infection may occur when a person is exposed to a source of fungi such as fungal spores in the air and/or soil. Frequently, however, a fungal infection occurs due to an imbalance in the normal mixture of microorganisms, i.e., normal flora, in the body tissue so that the presence of one or more fungal species increases resulting in infection. Depending on the fungal species it may spread from person to person, i.e., it may be contagious, or it may only affect the infected person. Anyone can be affected by a fungal infection, even people who are otherwise healthy. However, people with a deficiency in the immune system, patients treated with chemotherapy or immune suppressants, and patients suffering from diabetes or a lung disease are particularly susceptible to fungal infections.

Many fungal infections are widespread: For example, it is estimated that about 20-25% of the world's population suffers from a fungal skin infection. A further example of a common fungal infection is Candidiasis, which is a yeast infection due primarily to tissue overgrowth of *Candida albicans* and other species of *Candida* which are part of the normal flora. In babies, *Candida* can cause diaper rash. In women, vaginal infections involving *Candida* are very common causing pain, genital itching and/or vaginal discharge. Candidiasis in the vagina is commonly called a "vaginal yeast infection", "vaginal candidiasis", "vulvovaginal candidiasis", or "candidal vulvovaginitis."

Unfortunately, fungal infections are often difficult to treat which is due inter alia to the fact that fungi are eukaryotes, and the treatment may therefore also harm the eukaryotic host such as a human patient. A further challenge may be to perform the treatment to restore the normal flora including the fungi rather than completely eradicating the fungi. Moreover, it usually takes a week before relief of bothering symptoms such as itching, and rash takes place. For example, use of the antifungal medicine Clotrimazole requires about seven days of treatment before the fungal infection improves.

Also, side effects such as dehydration is a common issue when treating fungal infections of for example the intimate skin of the urogenital area, such as the lower abdomen with its highly fragile and sensitive mucous membrane.

Thus, there is a need for treatments allowing for mitigating and/or overcoming problems associated with fungal infections and the treatment thereof.

It is an object of the present disclosure to overcome or at least mitigate some of the problems associated with treatment of fungal infections.

SUMMARY

The present disclosure is directed to an aqueous composition comprising:
(a) at least one non-ionic cellulose ether, and
(b) benzoic acid within the range of from 0.2 wt % to 0.3 wt % based on the total weight of the composition,
wherein said composition has a viscosity of equal to or above 24 000 cP, an osmolality of from 100 to 400 mOsmol/kg, and a pH of from 3 to 5.

There is also provided an article as described herein comprising a composition as described herein.

There is also provided a composition as described herein for use in the treatment and/or prevention of a human fungal infection.

Further, there is provided a composition as described herein for use in the manufacturing of a product such as a medicinal product or medicament for the treatment and/or prevention of a human fungal infection.

Further, there is provided a method for treating and/or preventing a fungal infection, wherein said method comprises administration of an effective amount of a composition as described herein to a patient in need thereof.

Other features and advantages of the invention will be apparent from the following detailed description, examples, and from the claims.

DEFINITIONS

A "pH regulating agent" is any agent, such as a liquid agent, such as an aqueous liquid, which is able to regulate and/or maintain the pH of said pharmaceutical composition, wherein said pH is kept approximately in a selected range, which selected range is exemplified herein. Such a pH regulating agent can for example be a buffer, such as a citrate, lactate or phosphate buffer. A "buffer" is an ionic compound, usually a salt of a weak acid or base, added to a solution to resist changes in its acidity or alkalinity and thus stabilize its pH. A buffer solution is a solution containing such a compound. Other examples of pH regulating agents are organic and inorganic acids and bases, such as acetic acid, citric acid, phosphoric acid, hydrochloric acid and sodium hydroxide.

The cellulose ethers used in the composition disclosed in this document are non-ionic, with alkyl and/or hydroxyalkyl groups attached to the anhydroglucose units by ether linkages, which form hydroxyalkylalkylcelluloses, wherein the alkyl groups have from 1 to 4 carbon atoms.

Representative cellulose ethers for use in the pharmaceutical compositions according to the present invention are methylcellulose (MC), hydroxyethylmethylcellulose (HEMC), hydroxypropylmethylcellulose (HPMC), hydroxyethylethylcellulose (HEEC), and hydroxypropylcellulose (HPC). These polymers have substituents that are either nonpolar (e.g., methyl) or slightly polar (e.g., hydroxyethyl), which in combination with the hydrophilic cellulose backbone provide an amphiphilic polymer.

The benzoic acid used in the composition according to the present disclosure is used both as an antimicrobial preservative and as an active ingredient, i.e., an active pharmaceutical ingredient which may provide a fast reduction of the levels of fungi when used for treatment of a fungal infection.

The viscosity of the composition disclosed herein was measured at 20° C. according to European Pharmacopoeia 7.0, 2.2.10, e.g., using spindle viscometer Brookfield DV-I Prime with spindle number SC4-28 at 1 rpm (revolutions per minute) unless otherwise specified. The torque value should be ≥10% for the result to be stable and reliable. The Brookfield instrument will display a warning light if the torque value is <10%. The correct performance of the instrument was regularly checked with reference standards (oils with different viscosities) supplied by Brookfield. The viscosity is given in cP (centipoise).

By "composition" is in the context of the present document intended a composition suitable for medical use. The composition may also be denoted a "medical composition" or a "pharmaceutical composition".

By "osmolality" is meant the concentration of an osmotic solution when measured in osmol or milliosmol per 1 kg of solvent. It will be appreciated that 1 milliosmol per kg (i.e., mOsmol/kg) of solvent equals 1 mOsmolal.

The term "cP" stands for centipoise and is a unit for viscosity.

The term "wt %" stands for weight percent.

By room temperature is meant a temperature of about 20-25° C.

DESCRIPTION

The present disclosure provides an aqueous composition comprising:
(a) at least one non-ionic cellulose ether, and
(b) benzoic acid within the range of from 0.2 wt % to 0.3 wt % based on the total weight of the composition,
wherein said composition has a viscosity equal to or above 24 000 cP, an osmolality of from 100 to 400 mOsmol/kg, and a pH of from 3 to 5.

The present disclosure is based on the surprising finding that a composition as described herein allows for improved treatment of a human fungal infection such as a fungal infection involving one or more of the following fungi: *Aspergillus brasiliensis* and *Candida albicans*. Importantly, the levels of fungi may be lowered fast such as lowered within 24 hours of treatment. Additionally, the levels of fungi remain low also after seven days of treatment. While not wishing to be bound by any specific theory it is believed that the fast lowering of the levels of fungi may be linked to the amount of benzoic acid present in the composition, since a corresponding composition with a reduced amount of benzoic acid did not exhibit the same fast lowering of the levels of fungi. Of course, this fast onset of action is a significant benefit for patients in need of relief of bothering symptoms associated with the fungal infection such as pain, irritation and/or itching. In addition, the composition as disclosed herein prevents dehydration of the mucosal membrane upon use. Further, to add benzoic acid in this form, i.e., as in the composition as disclosed herein, to a patient in need thereof, is beneficial for the user since the composition as described herein is characterized by being safe and non-irritating to use.

The composition may have a viscosity of at least 38 000 cP, 40 000 cP, 45 000 cP, 47 000 cP, 50 000 cP, 52 000 cP, or 55 000 cP. For example, the composition may have a viscosity of from 24 000 cP to 100 000 cP, from 35 000 cP to 100 000 cP, from 38 000 cP to 100 000 cP, from 40 000 cP to 100 000 cP, from 45 000 cP to 100 000 cP, from 47 000 cP to 100 000 cP, from 50 000 cP to 100 000 cP, from 52 000 cP to 100 000 cP or from 55 000 cP to 100 000 cP.

The viscosity as defined in this document is determined as described above by measurement at 20° C. according to Ph. Eur. 2.2.10. The viscosity values referred to herein were measured at 1 rpm unless otherwise specified. The composition may have a viscosity of at least 38 000 cP, 40 000 cP, 45 000 cP, 47 000 cP, 50 000 cP, 52 000 cP, or 55 000 cP after storage at room temperature for six months. The storage stability of the composition as regards viscosity may be affected by the storage conditions. For example, storing the composition refrigerated and/or in glass containers may reduce the viscosity reduction during storage.

The composition described herein has an osmolality from 100 mOsmol/kg to 400 mOsmol/kg. Optionally, the composition as described herein has an osmolality from 100 mOsmol/kg to 200 mOsmol/kg. For instance, composition osmolality may be 100 mOsmol/kg, 150 mOsmol/kg, 200 mOsmol/kg or 400 mOsmol/kg. This has been found to provide a composition which is further effective against fungal infections. In addition, this has been found to provide a composition which is particularly adapted for preventing dehydration of the mucosal membrane upon use.

The pH of the composition disclosed herein may be within the range of from 3 to 5, such as from 3.1 to 4.8, such as from 3.6 to 4, such as from 3.7 to 3.9, such as from 3.6 to 3.8, such as from 3 to 3.8, such as from 3 to 3.5, or from 3 to 3.3. The pH may be regulated by the addition of a pH regulating agent to the composition. The pH regulating agent may e.g., be a buffer, such as a lactate or citrate buffer or an acid or base, such as hydrochloric acid or sodium hydroxide. The concentration of a buffer to be added to the composition may be from 50 mM to 300 mM, such as from 50 mM to 225 mM, or from 50 mM to 150 mM in an aqueous solution. For example, the concentration may be 50 mM, 150 mM, 225 mM or 300 mM. It should be noted that these values are not exact, meaning that they can vary slightly around the values provided. Depending on which pH is required and which buffer is used in the pharmaceutical composition, the concentration of the buffer will vary in accordance with the above. This has been found to provide a composition which is further effective against fungal infections. In addition, this has been found to provide a composition which is particularly adapted for preventing dehydration of the mucosal membrane upon use.

The composition described herein may have an osmolality of from 100 mOsmol/kg to 200 mOsmol/kg and a pH within the range of from 3.6 to 4, such as from 3.7 to 3.9, such as from 3.6 to 3.8.

The composition comprises benzoic acid in an amount from 0.2 wt % to 0.3 wt % based on the total weight of the composition. In particular, the benzoic acid may be added in an amount of 0.2 wt % based on the total weight of the composition. This has been found to provide a composition which is effective against fungal infections.

The non-ionic cellulose ether may be selected from the group consisting of methylcellulose (MC), hydroxypropylmethylcellulose (HPMC), hydroxypropylcellulose (HPC), hydroxyethylethylcellulose (HEEC) and hydroxyethylmethylcellulose (HEMC) and any combination of one or more thereof. For instance, the non-ionic cellulose ether may comprise or consist of hydroxypropylmethylcellulose (HPMC). This has been found to provide a thickening and stabilizing effect on the composition. Further, the composition comprising a hydrated non-ionic cellulose ether provides a lubricating effect when applied onto the vagina.

The amount of non-ionic cellulose ether used in the pharmaceutical composition may be selected so that the desired viscosity is obtained. As is known to the person skilled in the art of pharmaceutical development, the chain length of the non-ionic cellulose ethers is one parameter that affects the viscosity obtained, with shorter chain lengths providing a lower final viscosity when a certain concentration of non-ionic cellulose ethers are used than if the same concentration of non-ionic cellulose ethers with a longer chain length are used. As is also known to the person skilled in the art of pharmaceutical development, there is always a variation in the chain lengths in every batch of non-ionic cellulose ethers, which variation can be small or large. However, it is the mean chain length that affects the viscosity.

The composition described herein may comprise from 1 to 5% (w/w) of non-ionic cellulose ethers, such as 1.5, 2, 2.5, 3, 3.5, 4, or 4.5% (w/w) non-ionic cellulose ether. For instance, the composition may comprise from 2.5 to 3.5% (w/w) non-ionic cellulose ether. However, as mentioned above, due to the variation in chain lengths between different batches of non-ionic cellulose ethers, the actual amount of non-ionic cellulose ether must be adjusted to achieve the desired viscosity. This is however routine work for the person skilled in the art of pharmaceutical development.

The viscosity of the composition is equal to or above 24 000 cP. Due to this high viscosity of the composition described herein, it can be provided as a topical composition such as a gel, cream, foam, lotion or ointment. The high viscosity of the composition is beneficial since it makes it easier to handle and also leads to it remaining on or in the treatment site where it has been applied. This is particularly useful when the composition is applied in places where it may otherwise easily leave such as the vagina. It will be appreciated that the viscosity of the composition is considerably higher just after manufacture than after storage for some time. For example, the viscosity of the composition after manufacture may be about 50 000 cP. Storage of the composition at room temperature generally leads to a lowering of the viscosity. Therefore, it is preferred that the composition has a viscosity of at least 38 000 cP after manufacture so that storage such as storage at room temperature for 36 months does not lead to a viscosity below 24 000 cP.

Also, the composition as defined herein has good mucoadhesive properties. In general, mucoadhesive compositions interact with the mucus layer covering the mucosal epithelial surface, and mucin molecules and increase the residence time of the composition at the site of administration. Mucoadhesion describes the attractive forces between a composition and mucus or mucous membrane.

There are two main stages of the mucoadhesive process, the contact stage and the consolidation stage. The contact stage involves the initial wetting that occurs between the composition and the mucous membrane. This can occur mechanically by bringing together the two surfaces.

The consolidation stage affects the residence time of the composition on the surface and is governed mainly by attractive non-covalent interactions between the two surfaces but also by differences in osmotic pressure between the composition and the mucous membrane.

A low osmotic pressure of the composition described herein, that is a hypotonic composition, results in a flow of water from the composition to the mucous membrane. Without wishing to be bound by any specific theory, it is believed that the composition may exert at least part of its action by delivering water to the treatment site such as vaginal mucosa. This may be due to the composition's hypotonic properties associated with its low osmolality. By providing the composition as described herein with such a low osmolality that the composition is hypotonic, an improved composition preventing the mucosal membrane to de-hydrate upon use may be provided. This is an important effect since the mucosal membrane of for example the urogenital area is highly fragile and sensitive and easily becomes dehydrated when treated with conventional antifungals.

The pH of the aqueous composition described herein may be achieved by using a buffer system. Advantageously, the buffer system may comprise lactic acid and lactate such as sodium lactate, potassium lactate or ammonium lactate. Such a buffer system allows for restoring any imbalance of microorganisms associated with the fungal infection and/or for maintaining a normal balance of microorganisms in the treatment site. The lactic acid/lactate buffer system may provide a pH from 3.6 to 4, such as from 3.7 to 3.9, such as from 3.6 to 3.8.

Further, the amount of lactic acid in the aqueous composition described herein may be within the amount of from 40 mM to 60 mM, such as from 45 mM to 55 mM, such as 50 mM, in combination with added lactate, such as sodium lactate, potassium lactate or ammonium lactate to provide a pH within the range of from 3.6 to 4.0, such as within the range of from 3.7 to 3.9, such as from 3.6 to 3.8.

Additionally or alternatively, the buffer system may comprise citric acid and citrate such as sodium citrate. Such a citric acid/citrate buffer system may provide a pH of from 3.1 to 4.8.

The composition may or may not comprise an additional active pharmaceutical ingredient, such as drugs primarily delivered by intravaginal administration. For instance, the additional active pharmaceutical ingredient may be a pharmaceutical drug for treating and/or preventing a fungal infection. Accordingly, the composition described herein may be a pharmaceutical composition. Thus, there is provided a composition as described herein for use as a medicament.

In addition, when the composition is free from an additional active pharmaceutical ingredient the composition is non-cytotoxic. Also, as the composition comprises so few ingredients, the risk for adverse reactions against it is decreased.

When the composition does not comprise an additional pharmaceutically active ingredient, the composition may in particular not comprise oxytocin.

There is also provided an article comprising the composition described herein. For instance, the article may be a dispenser allowing for release of a desired amount of the composition. In a further example, the article may be a container or tube such as a pocket-sized container or tube made of metal and/or plastics. The article may be provided together with instructions for use such as instructions for use of the composition.

The composition described herein may be administered vaginally. Typically, 0.5-1.5 ml, such as about 1 ml of the composition is administered once daily, although it is possible to administer the composition twice daily or more than twice daily. The composition may be administered just prior going to bed. The administration is preferably done by using the article as disclosed herein.

The composition described herein may be administered to a patient in need thereof. For instance, the composition described herein may be administered to a patient in need of treatment and/or prevention of a fungal infection, such as a patient with a deficiency in the immune system, a patient treated with immune suppressant and/or a patient suffering from diabetes.

There is also provided a composition as described herein for use in the treatment and/or prevention of a human fungal infection.

There is also provided a method for treating and/or preventing a fungal infection, wherein said method comprises administration of an effective amount of a composition as described herein to a patient in need thereof.

The fungal infection described herein may involve *Candida* fungus. Additionally or alternatively, the fungal infection may involve one or more of the following: *Aspergillus brasiliensis* and *Candida albicans*. The fungal infection may be an oral fungal infection such as a fungal infection taking place in the oral cavity. For instance, the oral fungal infection may be oral candidiasis. Further, the fungal infection may be a non-oral fungal infection such as one or more of the following genital fungal infection, urinary tract infection, skin fungal infection. The genital fungal infection may involve the vagina and/or vulva. For instance, the genital fungal infection may be a vaginal fungal infection such as vaginal candidiasis. In a further example, the genital fungal infection may be a penile yeast infection. Further, the fungal infection may be a urinary tract infection.

The composition described herein may also be used in the treatment and/or prevention of bacterial vaginosis. Further, there is provided a use of a composition as described herein for the manufacture of a medicament for the treatment and/or prevention of bacterial vaginosis. There is also provided a method for treating bacterial vaginosis, said method comprising administering an effective amount of the composition to a patient in need thereof. This treatment and/or prevention of bacterial vaginosis may take place in combination with the treatment and/or prevention of the fungal infection described herein. Alternatively, this treatment and/or prevention of bacterial vaginosis may take place without treating and/or preventing a fungal infection as described herein. As used herein, bacterial vaginosis intends a vaginal inflammation involving overgrowth in the vagina of bacterial naturally found in the vagina. Symptoms of bacterial vaginosis usually include vaginal discharge, burning and/or itching.

When the fungal infection is an oral infection, it may be an infection taking place in the oral cavity. For example, the oral fungal infection may be oral candidosis. Further, the oral fungal infection may be associated with the use of dentures. In particular, the oral fungal infection may be associated with *Candida* such as *Candida albicans*. *Candida albicans* is believed to be highly infective due to high pathogenicity and good adherence properties.

When the fungal infection is a fungal skin infection it may superficial and/or local. For example, the fungal skin infection may take place in body areas that are warm, moist and/or poorly ventilated. For instance, the fungal infection may take place in the folds of the buttocks such as in diaper rash. Frequently, the fungus involved in fungal skin infections comprises *Candida* such as *Candida albicans*. Thus, the fungal skin infection may be skin candidiasis which may also be denominated cutaneous candidiasis.

There is also provided a composition as described herein for use in the treatment and/prevention of bacterial vaginosis.

The invention will be further described in the following examples, which do not limit the scope of the invention described in the claims.

EXAMPLES

General

The equipment used for mixing was a Unimix SRT 15. The hypromellose used was Benecel K15M Pharm.

Example 1: Pharmaceutical Composition Manufacturing of a First Composition

A first composition was prepared as follows. The components of Table 1 were mixed as follows. Purified water (1 371 g) was added to a container followed by lactic acid (33 g). Mixing was performed until a homogeneous solution, as indicated by visual inspection, was obtained. The pH of the homogenous solution was measured and found to be 2.72. The pH was adjusted to 3.72 by addition of a 5 M aqueous solution of NaOH. Thereafter, purified water was added (719.3 g) followed by benzoic acid (15 g) at a mixing speed of 4.5 rpm. Homogenization was activated for 125 s at a mixing speed of 4.5 rpm. Mixing was continued for 90 minutes. Then, visual inspection revealed that all benzoic acid was dissolved. The solution was allowed to assume room temperature, and then hypromellose (450 g) was added to the solution. The resulting solution was mixed at about 12° C. at a mixing speed of about 2.5 rpm for 121 minutes. During this time, the homogenizer was activated for about 1 minute. Thereafter, mixing was continued at a mixing speed of about 2.5 rpm at room temperature for 18 hours. The resulting gel was homogenous as shown by visual inspection. No lumps or air bubbles were present.

TABLE 1

| Component | Amount per batch (g) |
| --- | --- |
| Benzoic acid | 15 |
| Lactic acid | 33 |
| Sodium hydroxide 5M | q.s.* |
| Hypromellose (Benecel) | 450 |
| Purified water | q.s.** |

*To a pH of 3.75 (q.s. stands for quantum satis)
**To a final weight of 15 000 g Visual inspection showed that the gel was substantially clear. The viscosity was measured at 20° C. according to European Pharmacopoeia 7.0, 2.2.10 at 1-12 rpm as well as the pH was measured providing values shown in Table 2. The pH was 3.6.

TABLE 2

| Mixing speed in rpm | Viscosity value in cP |
| --- | --- |
| 1 | 62 500 cP |
| 3 | 50 167 cP |
| 5 | 43 800 cP |
| 10 | 35 100 cP |
| 12 | 32 833 cP |

Example 2: Storage Stability

The storage stability of the pharmaceutical composition of Example 1 was tested at a temperature of about 2-8° C. when kept in aluminum tubes. The storage stability was monitored by measurement of viscosity and pH as shown in Table 3.

TABLE 3

| | Viscosity and pH as a function of time after storage in aluminium tube at 2-8° C. | | | |
| --- | --- | --- | --- | --- |
| Analysis | Limits | Viscosity at 0* months | Viscosity at 6 months | Viscosity at 12 months |
| Viscosity at 1 rpm, cP | 1 rpm | 52 000 | 47 000** | 11 000** |
| pH | 3.4-4.2 | 3.6 | 3.6 | 3.6 |

*Initial results measured after 2 months of bulk storage
**Uncertain due to low torque value (<10%) during analysis As shown in Table 3, the viscosity of the pharmaceutical composition kept in the aluminum tube decreased with time, and in particular after six months' storage (i.e., after 8 months' storage from date of production).

Example 3: Pharmaceutical Composition Manufacturing of a Second Composition

Finely ground benzoic acid (0.2495 grams) was added to 249.87 grams of composition 1 (see Example 1). The resulting composition was stirred with a spatula and then allowed to stand at room temperature for about 24 hours. Thereafter, the composition was placed in an ultrasonic bath and subjected to sonication (2×15 minutes) at room temperature followed by stirring with a spatula. After the composition had been allowed to stand for 24 hours at room temperature it was observed that the benzoic acid had been entirely dissolved. Still, this composition was subjected to sonication in an ultrasonic bath (2×15 minutes) to provide a final composition which was clear as verified by ocular inspection.

Example 4: Antimicrobial Reduction Using the First Composition and the Second Composition, Respectively

Materials and Methods

Table 1 shows the products that were used, namely composition 1 and composition 2. Table 2 shows the media that were used. Table 3 shows the microorganisms that were tested.

TABLE 1

| Product used | | | | |
|---|---|---|---|---|
| Product | Package | Batch No | Amount | Sample No |
| Composition 1 36 g | Tube 36 g/unit | 1840241 | 20 g | BK480 |
| Composition 2 | bulk | ACA200108 | 20 g | BK481 |

TABLE 2

| Media used | |
|---|---|
| Medium | Batch No |
| 0.9% NaCl | 13NDP192 |
| Buffered NaCl Peptone (BNP) with 1% polysorbate 80 | 200108-2, 200218-1 |
| SDA (Sabouraud Dextrose Agar)[1] | 200109-1 |
| TSA (Soybean-casein Digest Agar)[1] | 1007655160 |

[1] The medium was tested for growth promotion with approved result

TABLE 3

| Microorganisms used | |
|---|---|
| Microorganism[1] | Reference number |
| Aspergillus brasiliensis | ATCC 16404 |
| Candida albicans | ATCC 10231 |
| Escherichia coli | ATCC 8739 |
| Pseudomonas aeruginosa | ATCC 9027 |
| Staphylococcus aureus | ATCC 6538 |

[1] The microorganisms were not more than 5 passages from the original master seed-lot.

Microorganism Preparation

Frozen stock suspensions of the microorganisms were used. Microorganisms were thawed and mixed before use. Media and incubation times were according to USP <51>.

Validation Study

A validation study was performed and approved in advance for the method suitability of the filtration method used in the test. The validation study was performed for both products.

The recovery of the inoculum should be between 50 and 200% for all microorganisms.

Method

The test for efficacy of antimicrobial preservation was performed on 20 g of the product which was mixed in sterile containers with $10^4$-$10^5$ cfu/mL of each microorganism, separately. As reference, representing day 0, an equal concentration of all microorganisms was added to one bottle each containing 20 mL of 0.9% NaCl. The references were 10-fold serial diluted and tested immediately in duplicates by the surface spread method.

The inoculated product was incubated at 20-25° C. for 7 days and tested after 6 hours, 24 hours and at day 7. 1g of the sample was mixed in 100 mL of BNP with 1% Tween 80. Different amounts (0.1, 1, and 10 mL) of the solution was filtrated and washed three times with 100 mL of 0.9% NaCl. The filters were then placed on Tryptone Soya Agar (TSA) plates for bacteria and Sabouraud Dextrose Agar (SDA) plates for fungi.

The plates were incubated for ≥72 hours at 30-35° C. for E. coli, P. aeruginosa and S. aureus and 20-25° C. for C. albicans 72 h) and A. brasiliensis (≥5 days), respectively. The total colony forming units were determined and the log reduction for each microorganism was calculated after the incubation.

Results

Results from the Validation Study

Results from the Validation study are presented in Table 4. All microorganisms grew within the specified limits. The method is adequate for detection of microorganisms in 0.1 mL of the product per plate.

TABLE 4

Results of viable count of inocula and the recovery relative to the positive reference for each microorganism

| | Viable count product (cfu/plate) Sample No | | Viable count reference | Recovery, product/reference (%) Sample No | |
|---|---|---|---|---|---|
| Microorganism | BK480 | BH481 | (cfu/plate) | BK480 | BH481 |
| Aspergillus brasiliensis | 43, 51 | 48, 50 | 48, 38 | 109 | 114 |
| Candida albicans | 48, 46 | 51, 37 | 37, 38 | 125 | 117 |
| Escherichia coli | 65, 52 | 52, 56 | 46, 51 | 121 | 111 |
| Pseudomonas aeruginosa | 29, 21 | 21, 30 | 31, 26 | 88 | 89 |
| Staphylococcus aureus | 49, 36 | 25, 27 | 38, 40 | 109 | 67 |

Results from Antimicrobial Effectiveness Testing

Results from the test are presented in Tables 5 to 8.

TABLE 5

Results of viable counts of each microorganism in the presence of the product, presented as cfu/mL and $\log_{10}$ values ($\log_{10}$ to the mean value of the cfu/mL) for the product Vagivital (batch1840241).

| Product: Composition 1, 36 g | | | | | | Sample No: BK480 | | | | |
|---|---|---|---|---|---|---|---|---|---|---|
| | Fungi | | | | Bacteria | | | | | |
| Sampling | *Aspergillus brasiliensis* | | *Candida albicans* | | *Escherichia coli* | | *Pseudomonas aeruginosa* | | *Staphylococcus aureus* | |
| time | cfu/mL | $\log_{10}$ | cfu/mL | $\log_{10}$ | cfu/mL | $\log_{10}$ | cfu/mL | $\log_{10}$ | cfu/mL | $\log_{10}$ |
| Initial calculated count (day 0)[1] | $13 \times 10^4$ $7 \times 10^4$ | 5.00 | $69 \times 10^4$ $59 \times 10^4$ | 5.81 | $81 \times 10^4$ $70 \times 10^4$ | 5.88 | $73 \times 10^4$ $64 \times 10^4$ | 5.84 | $30 \times 10^4$ $21 \times 10^4$ | 5.41 |
| 6 hours | $5 \times 10^5$ $5 \times 10^5$ | 5.70 | $115 \times 10^3$ $183 \times 10^3$ | 5.17 | $0 \times 10^1$ $0 \times 10^1$ | <1.00 | $0 \times 10^1$ $0 \times 10^1$ | <1.00 | $0 \times 10^1$ $0 \times 10^1$ | 1.00 |
| 24 hours | $5 \times 10^5$ $5 \times 10^5$ | 5.70 | $73 \times 10^3$ $77 \times 10^3$ | 4.88 | $0 \times 10^1$ $0 \times 10^1$ | <1.00 | $0 \times 10^1$ $0 \times 10^1$ | <1.00 | $0 \times 10^1$ $0 \times 10^1$ | <1.00 |
| 7 days | $0 \times 10^1$ $0 \times 10^1$ | <1.00 | $0 \times 10^1$ $0 \times 10^1$ | <1.00 | $0 \times 10^1$ $0 \times 10^1$ | <1.00 | $0 \times 10^1$ $0 \times 10^1$ | <1.00 | $1 \times 10^1$ $0 \times 10^1$ | <1.00 |

[1] Results from the reference.

TABLE 6

Results of viable counts of each microorganism in the presence of the product, presented as cfu/mL and $\log_{10}$ values ($\log_{10}$ to the mean value of the cfu/mL) for the product Vagivital 0.2% benoic acid (batch ACA200108).

| Product: Composition 2 | | | | | | Sample No: BK481 | | | | |
|---|---|---|---|---|---|---|---|---|---|---|
| | Fungi | | | | Bacteria | | | | | |
| Sampling | *Aspergillus brasiliensis* | | *Candida albicans* | | *Escherichia coli* | | *Pseudomonas aeruginosa* | | *Staphylococcus aureus* | |
| time | cfu/mL | $\log_{10}$ | cfu/mL | $\log_{10}$ | cfu/mL | $\log_{10}$ | cfu/mL | $\log_{10}$ | cfu/mL | $\log_{10}$ |
| Initial calculated count (day 0)[1] | $13 \times 10^4$ $7 \times 10^4$ | 5.00 | $69 \times 10^4$ $59 \times 10^4$ | 5.81 | $81 \times 10^4$ $70 \times 10^4$ | 5.88 | $73 \times 10^4$ $64 \times 10^4$ | 5.84 | $30 \times 10^4$ $21 \times 10^4$ | 5.41 |
| 6 hours | $4 \times 10^3$ $1 \times 10^3$ | 3.40 | $60 \times 10^3$ $69 \times 10^3$ | 4.81 | $0 \times 10^1$ $0 \times 10^1$ | <1.00 | $0 \times 10^1$ $0 \times 10^1$ | <1.00 | $0 \times 10^1$ $0 \times 10^1$ | <1.00 |
| 24 hours | $0 \times 10^1$ $0 \times 10^1$ | <1.00 | $1 \times 10^2$ $2 \times 10^1$ | 1.78 | $0 \times 10^1$ $0 \times 10^1$ | <1.00 | $0 \times 10^1$ $0 \times 10^1$ | <1.00 | $0 \times 10^1$ $0 \times 10^1$ | <1.00 |
| 7 days | $0 \times 10^1$ $0 \times 10^1$ | <1.00 | $0 \times 10^1$ $0 \times 10^1$ | <1.00 | $0 \times 10^1$ $0 \times 10^1$ | <1.00 | $0 \times 10^1$ $0 \times 10^1$ | <1.00 | $0 \times 10^1$ $0 \times 10^1$ | <1.00 |

[1] Results from the reference.

TABLE 7

The log reduction of *Aspergillus brasiliensis*, *Candida albicans* and bacteria during antimicrobial preservation test. Results are presented as $\log_{10}$ differences between day 0, 6 hours, 24 hours and day 7, respectively. (Day 0 = initial calculated count).

| Composition 1, 36 g and Composition 2 Comparison time | | Sample No: BK480 $\text{Log}_{10}$ reduction | Sample No: BK481 $\text{Log}_{10}$ reduction |
|---|---|---|---|
| *Aspergillus brasiliensis* | 6 hours | [1] | 1.6 |
| | 24 hours | [2] | >4.0 |
| | 7 days | >4.0 | >4.0 |
| *Candida albicans* | 6 hours | 0.6 | 1.0 |
| | 24 hours | 0.9 | 4.0 |
| | 7 days | >4.8 | >4.8 |
| Bacteria | 6 hours | >4.4 | >4.4 |
| | 6 hours | >4.4 | >4.4 |
| | 7 days | >4.4 | >4.4 |

[1] [2] It was not possible to count the plates due to that the colonies were grown together, and the growth was estimated to 500 cfu and no log reduction can be shown. Thus, no logarithmic reduction was observed.

Conclusions

The efficacy of antimicrobial reduction was performed on composition 1 and composition 2, respectively, following the analysis procedures for the antimicrobial effectiveness test USP <51> for oral preparations. With no acceptance criteria, was the antimicrobial preservation evaluated by determining the log reduction of microorganisms over time. The $\log_{10}$ reductions for bacteria, fungi and yeast had a decrease of >4.0 after 7 days for both compositions.

The microorganisms *Aspergillus brasiliensis* and *Candida albicans* had a longer survival in both compositions.

For *A. brasiliensis* in composition 1, there was no $\log_{10}$ reduction after 24 hours. However, in composition 2, a $\log_{10}$ reduction of 1.6 and >4.0 was achieved after 6 hours and 24 hours respectively.

For *Candida albicans* a similar pattern was seen, there was a slower reduction of colony forming units over 24 hours in composition 1 compared to composition 2.

An inoculum of bacteria in both, composition 1 and composition 2, the reduction effect was achieved already after 6 hours ($\log_{10}$ reductions>4.4) and showed no change in colony forming units over 7 days.

The result of the antimicrobial reduction test for two composition 1 and composition 2, respectively, showed that after 7 days none of the tested microorganism could be detected.

The efficacy of antimicrobial reduction for composition 1 and composition 2 showed that both compositions reduced the number of microorganisms tested. Importantly, composition 2 had a faster onset of reduction of the microorganisms tested.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Unless expressly described to the contrary, each of the preferred features described herein can be used in combination with any and all of the other herein described preferred features.

The invention claimed is:

1. A method for the treatment and/or prevention of a human fungal infection, said method comprising administering to a patient in need thereof an effective amount of an aqueous composition comprising:
    (a) at least one non-ionic cellulose ether, said at least one non-ionic cellulose ether being hydroxypropylmethylcellulose (HPMC), and
    (b) an active pharmaceutical agent being benzoic acid within the range of from 0.2 wt % to 0.3 wt % based on the total weight of the composition,
    wherein said composition has a viscosity equal to or above 24 000 cP, an osmolality of from 100 to 400 mOsmol/kg, and a pH of from 3 to 5,
    wherein the aqueous composition does not comprise an additional active pharmaceutical agent other than benzoic acid.

2. The method according to claim 1, wherein said composition has an osmolality of from 100 to 200 mOsmol/kg.

3. The method according to claim 1, wherein said composition has an osmolality of from 200 to 400 mOsmol/kg.

4. The method according to claim 1, wherein said composition has a viscosity of from 24 00 to 100 000 cP.

5. The method according to claim 1, wherein said composition has a pH within the range of from 3.1 to 4.8.

6. The method according to claim 1, wherein the pH is achieved using a buffer system comprising (i) lactic acid and lactate and/or (ii) citric acid and citrate.

7. The method according to claim 6, wherein the pH is achieved using a buffer system comprising lactic acid and lactate wherein the lactic acid is present in the composition in an amount of from 40 mM to 60 mM and the pH is within the range of from 3.6 to 4.

8. The method according to claim 1, wherein the human fungal infection involves *Candida* fungus.

9. The method according to claim 1, wherein the human fungal infection involves one or more of the following fungi: *Aspergillus brasiliensis* and *Candida albicans*.

10. The method according to claim 1, wherein the human fungal infection is selected from one or more of the following: a genital fungal infection, an urinary tract infection, an oral fungal infection, a skin fungal infection, and a nail fungal infection.

11. The method according to claim 10, wherein the human fungal infection is the genital fungal infection, wherein the genital fungal infection is a vaginal fungal infection.

12. The method according to claim 10, wherein the human fungal infection is the urinary tract infection.

13. The method according to claim 10, wherein the human fungal infection is the oral fungal infection, wherein the oral fungal infection is oral candidiasis.

14. The method according to claim 10, wherein the human fungal infection is the skin fungal infection, wherein the skin fungal infection is skin candidiasis.

15. The method according to claim 1, wherein the method comprises administering vaginally an amount of from 0.5 to 1.5 ml of the composition, wherein the composition is administered once daily for 7 days.

* * * * *